United States Patent [19]

Gautier et al.

[11] Patent Number: 4,473,710

[45] Date of Patent: Sep. 25, 1984

[54] PROCESS FOR THE SYNTHESIS OF TERTIARY PHOSPHINE OXIDES, AND NEW TERTIARY PHOSPHINE OXIDES

[75] Inventors: Jean-Claude C. G. Gautier, Ablon Sur Seine; Sammy H. Chevalier, Paris; Claude R. A. Soriaux, Athis-mons, all of France

[73] Assignee: Societe Nationale des Poudres et Explosifs, Paris, France

[21] Appl. No.: 387,354

[22] Filed: Jun. 11, 1982

[30] Foreign Application Priority Data

Jun. 26, 1981 [FR] France ................ 81 12593

[51] Int. Cl.³ ........................... C07F 9/53
[52] U.S. Cl. ........................... 568/15; 568/14
[58] Field of Search .................. 568/14, 15

[56] References Cited

U.S. PATENT DOCUMENTS

| | | | |
|---|---|---|---|
| 3,975,447 | 8/1976 | Knoth et al. | 568/14 |
| 4,020,110 | 4/1977 | Lippsmeier et al. | 568/14 |
| 4,053,518 | 10/1977 | Weston et al. | 568/14 |
| 4,061,681 | 12/1977 | Hillard et al. | 568/14 |
| 4,064,104 | 12/1977 | Mrowca | 568/14 X |
| 4,365,094 | 12/1982 | Boileau et al. | 568/14 |

OTHER PUBLICATIONS

Chemical Abstracts 89, 109949e, (1978).
Chemical Abstracts 93, 211938v, (1980).
Chemical Abstracts 64, 11243e, (1966).
Chemical Abstracts 71, 50076r, (1969).
Chemical Abstracts, 87, 200633s, (1977).

*Primary Examiner*—Helen M. S. Sneed
*Attorney, Agent, or Firm*—Bucknam and Archer

[57] ABSTRACT

The invention relates to the synthesis of tertiary phosphine oxides and also to certain tertiary phosphine oxides.

According to the invention, an organic phase containing a halogenomethyl derivative, an hydroxymethylphosphine oxide and a phase transfer catalyst is reacted, in an organic medium, with an aqueous phase containing an inorganic base. The halogenomethyl derivative can be a micromolecule or a macromolecule.

Tertiary phosphine oxides are substances which are useful, in particular, in fireproofing, in hydrometallurgy and in the field of plant protection.

15 Claims, No Drawings

PROCESS FOR THE SYNTHESIS OF TERTIARY PHOSPHINE OXIDES, AND NEW TERTIARY PHOSPHINE OXIDES

The invention forming the subject of the present application relates to the synthesis of tertiary phosphine oxides. The present application relates, in particular, to the invention described and claimed in U.S. Ser. No. 213,212 which has now issued as U.S. Pat. No. 4,365,094.

In the past, a very wide variety of processes have been proposed for the synthesis of tertiary phosphine oxides.

Some of these processes use a Grignard reagent together either with phosphorus oxychloride, as in French Pat. No. 2,159,716, or with a mixture of phosphorus trichloride and oxygen, as in French Pat. No. 1,399,743, or with a phosphonyl chloride, as in U.S. Pat. No. 3,258,492, or also with a dialkyl phosphite and an organic halide, as in French Pat. No. 2,346,361.

Other processes use a technique involving thermal decomposition, for example of the product resulting from the addition of a dialkyl phosphite oxide onto an α-olefine, as in German Pat. No. 1,912,708, of a quaternary phosphonium halide, as in French Pat. No. 2,316,244, of a hydroxylic quaternary phosphonium halide, as in U.S. Pat. No. 3,997,611, or also of a tertiary hydroxymethylphosphine, as in U.S. Pat. No. 4,020,110.

Further processes involve phosphorus and an alkyl iodide in the presence of iodine, as in French Pat. No. 2,352,824.

These known processes are characterised by being somewhat expensive, by the existence of secondary reactions which are difficult to control, and by the use of drastic operating conditions, especially as regards the temperature and the solvents, which must be dry. Furthermore, they do not make it possible easily to obtain phosphine oxides of the type RRR'PO, in particular those in which R' is a polymeric chain of high molecular weight.

The process of synthesis forming the subject of U.S. Pat. No. 4,365,094 is a process for the synthesis of tertiary phosphine oxides from a dialkylphosphine oxide, characterised in that a secondary phosphine oxide is reacted with a halogenomethyl derivative in an organic medium, in an aqueous phase containing an inorganic base, and in the presence of a phase transfer catalyst, with stirring.

According to the present invention, it has been found that the process forming the subject of U.S. Pat. No. 4,365,094 is applicable not only to a simple secondary phosphine oxide but also to an hydroxymethylphosphine oxide. Thus the process according to the present invention proceeds according to the reaction scheme hereinbelow:

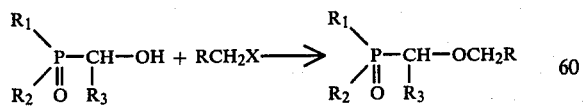

The process according to the present invention therefore consists of a process for the synthesis of tertiary phosphine oxides from a dihydrocarbylphosphine oxide, characterised in that an hydroxymethylphosphine oxide is reacted with a halogenomethyl derivative in a water-immiscible organic medium, in the presence of an aqueous phase containing an inorganic base, and in the presence of a phase transfer catalyst, with stirring.

According to the invention, the hydroxymethylphosphine oxides used have the general formula:

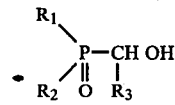

in which $R_1$ and $R_2$ are identical or different and are a linear or branched alkyl group containing from 1 to 18 carbon atoms, preferably from 1 to 12 carbon atoms, or a phenyl group. Particularly suitable phosphine oxides which may be mentioned are diethyl-, di-n-propyl-, di-n-butyl-, di-n-hexyl-, di-(2-ethylhexyl)-, di-n-octyl-, di-n-dodecyl-, methyloctyl-, ethylbutyl-, ethylheptyl-, ethylnonyl-, propyloctyl- and diphenyl-phosphine oxides and the like. $R_3$ is a hydrogen atom or alternatively a group of the formula $-CH_2-R_4$, in which $R_4$ is a hydrogen, a linear or branched alkyl group containing from 1 to 11 carbon atoms or alternatively a phenyl group.

Halogenomethyl derivatives which fall well within the scope of the invention are, in particular, those of the general formula $XCH_2R$, in which: X is a chlorine or bromine atom and R is a group $-CH=CHY$, in which Y is a hydrogen atom, a phenyl group or a group $-CH_2X$, in which X has one of the meanings indicated above, or alternatively R is a group

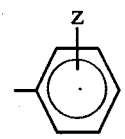

in which Z is a hydrogen atom, a $C_1$ to $C_4$ alkyl group, a vinyl group, a halogen atom, a group $-CH_2X$ or a group

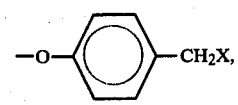

X having one of the meanings indicated above, or alternatively R is an alkyl chain containing from 1 to 12 carbon atoms, which is optionally substituted by at least one nitrile or epoxy group, or alternatively R is a phenyl group forming part of a random copolymer chain containing styrene and a p-halogenomethylstyrene, which has a molecular weight of between 500 and 1,000,000 and comprises x and y units

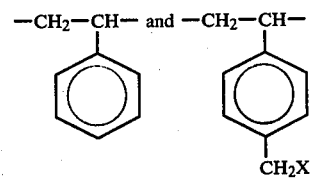

respectively, x and y being integers such that the ratio x:y is between 100:1 and 0:1, or alternatively R is a phenyl group forming part of a random copolymer chain containing styrene and a halogenomethylstyrene, which is partially crosslinked, is referred to as a Merrifield resin, has a molecular weight of between 1,000 and 1,000,000 and comprises x, y and z units

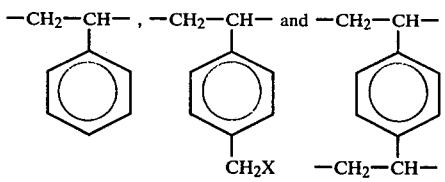

respectively, x, y and z being integers such that the ratio x:y is between 100:1 and 0:1 and such that the ratio z:y is between 1:25 and 1:5.

It is preferred to use a halogenomethyl derivative which, in isolation, is not sensitive to strong inorganic bases, that is to say a derivative which, when brought by itself into the presence of a base of this type, does not react or degrade rapidly.

The organic solvent used within the scope of the invention must be a common solvent for the hydroxymethyldihydrocarbylphosphine oxide and for the halogenomethyl derivative, must not be miscible with the alkaline aqueous phase and must preferably be slightly polar or non-polar, that is to say it must have a dielectric constant of less than 8 at 20° C. It is immaterial whether the solvent is protic or aprotic. Suitable solvents which may be mentioned are aromatic solvents, such as benzene, toluene and xylenes, and aliphatic solvents. Mixtures of solvents are also suitable. It is also possible to carry out the reaction in bulk, without a solvent.

The aqueous alkaline phase must contain an amount of inorganic alkaline base which is at least equal to the stoichiometric amount for the reaction, which consists overall of a condensation with the release of one molecule of hydrohalic acid per molecule of halogenomethyl derivative.

In practice, the aqueous alkaline phase must contain from 30% to 60% by weight of an inorganic base. The latter is preferably sodium hydroxide or potassium hydroxide, although other bases, such as lime, can be used.

The ratio of the volume of aqueous phase to the volume of organic phase is not highly critical, but in practice is between the extreme values of 5:1 and 1:10. It is desirable to stir the reaction medium so as to promote contact between the organic and aqueous phases. Vigorous stirring has the effect of considerably accelerating the reaction rate.

The reaction is not sensitive to pressure, wherefore it is conveniently carried out under atmospheric pressure. On the other hand, the temperature is a critical factor because, below 0° C., the reaction is extremely slow, or even non-existent, and above 90° C., the reaction is in practice very difficult to carry out successfully and is accompanied by degradation of the products formed. A temperature between 40° and 70° C. generally gives the best results. The reaction is advantageously carried out under an inert atmosphere consisting of argon or nitrogen. If it is desired to obtain a high yield, relative to the halogen derivative (or relative to the phosphine oxide), it is important to employ an amount of hydroxymethylphosphine oxide (or, respectively, of halogenomethyl derivative) which is at least equal to the stoichiometric amount, relative to the halogenomethyl derivative (or, respectively, relative to the hydroxymethylphosphine oxide).

However, although the molar ratio P/Cl is advantageously greater than 1, a value of more than 1.5 is to no advantage, except in the case where the halogenomethyl derivative is a resin, in particular of the random copolymer type indicated above.

As regards the concentration of the reactants in the organic phase, it is in practice between 1 and 20% by weight, relative to the solvent, and between 0.1 and 10% if the reactant is a polymer. However, it is also possible to carry out the reaction in bulk.

The reaction time varies from a few tens of minutes to a few tens of hours, depending on the temperature used and depending in particular on the nature of the phase transfer catalyst used.

The phase transfer catalysts of which the use is absolutely essential within the scope of the present invention are those conventionally used in reactions involving phase transfer catalysis. Two groups of these catalysts can be distinguished.

The first group comprises ionic phase transfer catalysts, which include the quaternary ammonium, phosphonium or arsonium salts of the general formula:

$$A_1A_2A_3A_4Y^+.X^-$$

in which $Y=N$, P or As, $A_1$, $A_2$, $A_3$ and $A_4$ are identical or different and are preferably $C_1$ to $C_8$ alkyl groups, benzyl groups or polymer chains, and $X^-$ is an anion. Preferably, $X^-$ is a halide, carboxylate, hydrogensulphate or hydroxide anion. The second group comprises non-ionic complexing agents, which include polyethylene oxides, crown ethers and cryptands. Crown ethers are macrocyclic polyethers in which certain oxygen atoms can be substituted by sulphur atoms, while cryptands are macropolyheterocyclic compounds comprising polyether heterocyclic rings in which certain oxygen atoms can be replaced by sulphur, the said heterocyclic rings being bridged by nitrogen atoms. These complexing agents have the property of forming, with alkali metal and alkaline earth metal cations, complexes possessing an extremely high stability constant. They are extensively described in Jean-Marie LEHN, Design of Organic Complexing Agents—Strategies towards Properties, Structure and Bonding, Volume 16, Springer Verlag (1973), in an article by E. VOGTLE and E. WEBER, published in Kontakte, Volume 1, pages 11 to 31 (1977), and entitled Neutrale Organische Komplexliganden und ihre Alkalikomplexe—Kronenäther, Cryptanden, Podanden (Neutral Organic Complexing Ligands and their Alkali Metal Complexes—Crown Ethers, Cryptands, Podands), and also in French Pat. Nos. 2,201,304 and 2,398,079. The crown ethers and the cryptands can be used either in the form of free molecules or in a form which is fixed to a polymer. However, this latter solution to the problem is not recommended when the halogenomethyl derivative is itself a polymer. Amongst the crown ethers and the cryptands, it is preferred to use those which form, with the cation of the alkali metal base employed, complexes having a particularly high stability constant. The complexing agents of this type which are particularly preferred are well known to those skilled in the art. Reference may advantageously be made to the article by C. Kappenstein published in Bulletin de la Société Chimique de France, No. 1-2, pages 89 to 109 (1974). Thus, if sodium hydroxide is employed in the aqueous phase, it is advantageous to use 1,4,7,10,13,16-hexaoxacyclooctadeca-2,11-diene, or dibenzo-18-crown-6 according to the nomenclature of Pedersen, J.Amer.Chem.Soc., 1967, 89, page 7,017, cyclohexyl-15-crown-5, 18-crown-6 and dicyclohexyl-18-crown-6, or alternatively the cryptands <222> and <221>, designated according to the nomenclature of J. M. LEHN (op. cit.) and Kappenstein (op. cit.). Potassium hydroxide is advantageously used in association with 18-crown-6, dicyclohexyl-18-crown-6 and cyclohexyl-18-crown-6, and <222>, <221> and <322>. Finally, if lime is used, the conditions are substantially the same as in the case of Na+ and it is advantageous to employ 18-crown-6 or dicyclohexyl-18-crown-6, or alternatively <222> or <221>, or alternatively the cryptands, fixed to a polymer, marketed by MERCK under the names Kryptofix <222> B polymer or Kryptofix <221> B polymer, in which the polymer residue is derived from a Merrifield resin. Many other crown ethers or cryptands are perfectly suitable within the scope of the invention, but these are compounds which give the impression of being laboratory curiosities.

Although the macroheterocyclic complexing agents generally prove wholly satisfactory within the scope of the invention, the quaternary ammonium salts, which are at least as effective and much less expensive, are preferred thereto as a general rule. As regards the phosphonium or arsonium salts, their activity is generally identical to that of the corresponding quaternary ammonium salts, but, on the other hand, they are substantially more expensive.

The amount of catalyst to be used is of the order of at least 1 mol %, relative to the halogen contained in the halogenomethyl derivative. Advantageously, a proportion of about 5 mol % will in fact be used. An excess of catalyst of more than 10 mol % appears to be neither disadvantageous nor advantageous.

It must be noted that it is conventionally acknowledged in the field of phase transfer catalysis (Makosza et al., J. Org. Chem. 43, 4,682 (1978)) that sodium carbonate and potassium carbonate, associated with a phase transfer catalyst such as dicyclohexyl-18-crown-6, constitute excellent bases for this kind of reaction. It has been shown that, within the scope of the invention, these associations have on the whole a moderate activity, because they only result in moderate to low yields, in particular in the case of polymerised halogenomethyl derivatives. This surprising phenomenon has not been explained. Once the reaction is complete, the reaction medium is cooled and the organic phase is separated from the aqueous phase and then treated. This treatment can consist in washing with a dilute acid solution, if appropriate after dilution of the said organic phase with an organic solvent. In the case where the halogenomethyl derivative is a polymer, this treatment can also consist in first precipitating the mixture in methanol and in purifying the precipitate by successive dissolutions in chloroform and reprecipitations in methanol.

The hydroxymethyldihydrocarbylphosphine oxides used within the scope of the present invention can be obtained with the aid of several well-known methods. The most general of these methods consists in adding one molecule of aldehyde to one molecule of the dihydrocarbylphosphine oxides used in U.S. Pat. No. 4,365,094, according to the reaction:

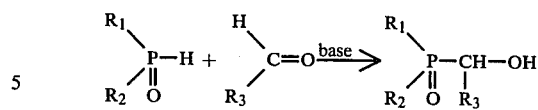

Another method, which is more specific for hydroxymethylphosphine oxides and monomethylphosphine oxides, is described in U.S. Pat. No. 4,028,421 and consists of carrying out the thermal rearrangement of a tertiary bis-(hydroxymethyl)-phosphine:

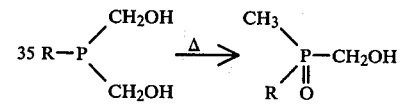

The yields obtained by the process according to the invention are generally extremely high, in particular when starting from halogenomethyl micromolecules, in which case the said yields are regularly of the order of 95 to 100%. However, all other things being equal, the reaction is more facile with the reactants in which $R_3=H$ than with those in which $R_3$ is a hydrocarbyl group. In the case of resins, it is possible easily to modify the degree of substitution between 10 and 90% by varying the solvent used and especially the catalyst used, and also by varying the reaction time and the temperature.

The invention also relates to the new industrial products of the general formula:

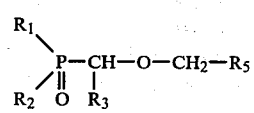

in which $R_1$ and $R_2$ are identical or different and are a linear or branched alkyl group containing from 1 to 18 carbon atoms, preferably from 1 to 12 carbon atoms, or a phenyl group, $R_3$ is a hydrogen atom or a group —$CH_2$—$R_4$, in which $R_4$ is a linear or branched alkyl group containing from 1 to 11 carbon atoms, a hydrogen atom or alternatively a phenyl group, and $R_5$ is chosen from the group comprising:

(a) a phenyl group forming part of one of the units

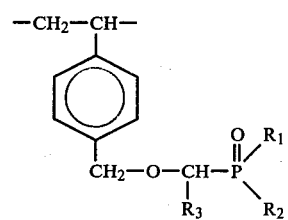

of a random copolymer derived from a random copolymer of styrene and a p-halogenomethylstyrene, which has a molecular weight of between 550 and 1,100,000 and comprises x and y units

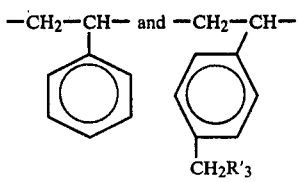

respectively, x and y being integers such that the ratio x:y is between 100:1 and 0:1, 20 to 90% by number of the R₃' groups being a group

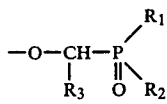

and 10 to 80% being a chlorine or bromine atom, (b) a phenyl group forming part of one of the units

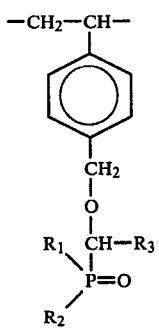

of a random copolymer derived from a random copolymer of styrene and a p-halogenomethylstyrene, which is partially crosslinked, is referred to as a Merrifield resin, has a molecular weight of between 1,100 and 1,100,000 and comprises x, y and z units

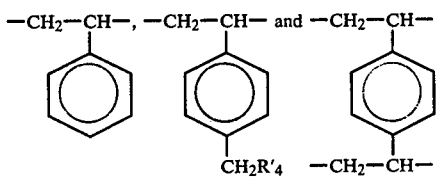

respectively, x, y and z being integers such that the ratio x:y is between 100:1 and 0:1 and such that the ratio z:y is between 1:25 and 1:5, 20 to 95% by number of the R₄' groups being groups

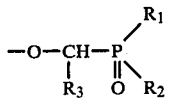

and 5 to 80% being chlorine or bromine atoms, or (c) a group

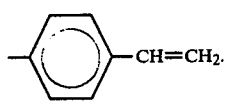

Particularly preferred products according to the invention are those which carry n-octyl radicals as $R_1$ and $R_2$ and in which $R_3$=H or —CH₂—R₄, in which $R_4$ is a linear $C_3$ to $C_8$ alkyl radical.

The products according to the invention are applied, in particular, in plant-protection formulations, as fireproofing compounds and as extraction agents.

The invention is further illustrated by the non-limiting examples which follow, which are carried out under a nitrogen atmosphere unless expressly stated to the contrary.

EXAMPLE 1

In a 4 liter reactor surmounted by a condenser and a thermometer and fitted with a mechanical stirrer, 273 g of dioctylphosphine oxide (DOPO), prepared by condensing diethyl phosphite with octyl-magnesium chloride, are heated under reflux for 8 hours with 290 cm³ of a 35% strength by weight aqueous solution of formaldehyde, 40 g of sodium bicarbonate, 6.2 g of potassium carbonate and 2.5 liters of ethanol.

After the alcohol has been evaporated off, the organic compounds are dissolved in methylene chloride (1 liter), the solution is washed with water, dried over MgSO₄ and filtered and the filtrate is evaporated. This yields 96% of hydroxymethyl-DOPO.

IR: P=O: 1,140 cm⁻¹; OH: 3,200 cm⁻¹.

NMR: broad signal at 0.85 ppm (6 protons) for the —CH₃; broad signal at 1.3 ppm (24 protons) for the —CH₂. broad signal at 1.55 ppm (4 protons) for the

broad signal at 3.65 ppm (2 protons) for the —CH₂—OH.

1.5 kg of a 50% strength aqueous solution of sodium hydroxide, 15 g of tetrabutylammonium hydrogensulphate (TBAH) and a mixture of 1 mol of hydroxymethyl-DOPO (304 g) and 1 mol (137 g) of n-bromobutane in 2.5 liters of toluene are placed in a 4 liter reactor surmounted by a condenser and a thermometer and fitted with a mechanical stirrer.

The mixture is stirred vigorously at 70° C. for 4 hours.

After settling, the phases are separated, the organic phase is evaporated and the residue is taken up in 1 liter of methylene chloride. After washing with water (NaCl being added in order to facilitate the settling), the solution is dried over magnesium sulphate and filtered and the filtrate is evaporated. This yields 325 g of di-n-octyl-n-butyloxymethyl-phosphine oxide.

IR: P=O: 1,172 cm⁻¹.

NMR: broad signal at 0.87 ppm (9 protons) for the —CH₃; broad signal at 1.27 ppm (28 protons) for the —CH₂—; broad signal at 1.61 ppm (4 protons) for the —CH₂—P; triplet at 3.47 ppm (2 protons) for the —CH₂—O—; doublet at 3.72-3.6 ppm (2 protons) for the

EXAMPLES 2 TO 7

The procedure of Example 1 is used on different starting materials, under substantially identical temperature and time conditions.

DOPO was used in Examples 2 to 5 and di-n-hexylphosphine oxide was used in Examples 6 and 7.

n-Octyl bromide was used in Examples 2 and 6, n-butyl bromide in Example 4 and n-octyl, n-butyl and 2-ethylhexyl chlorides in Examples 3, 5 and 7 respectively.

The results obtained, and also the special conditions used, are reported in the following table:

| Example | $R_1, R_2$ | $CH_2R_4$ | X | °C. | Time (hours) | Yield |
|---|---|---|---|---|---|---|
| 2 | n $C_8H_{17}$— | n $C_8H_{17}$— | Br | 70° C. | 4 | 92% |
| 3 | n $C_8H_{17}$— | n $C_8H_{17}$— | Cl | 70° C. | 5 | 35% |
| 4 | n $C_8H_{17}$— | n $C_4H_9$— | Br | 70° C. | 4 | 90% |
| 5 | n $C_8H_{17}$— | n $C_4H_9$— | Cl | 75° C. | 5½ | 75% |
| 6 | n $C_6H_{13}$— | n $C_8H_{17}$— | Br | 70° C. | 1 | 80% |
| 7 | n $C_6H_{13}$— | —CH$_2$CH(C$_2$H$_5$)(C$_4$H$_9$) | Cl | 85° C. | 3 | 65% |

The poor result of Example 3 is due to the premature thermal decomposition of the TBAH. A yield of 75% can be obtained in this case by adding a further 10 g of TBAH after a reaction time of 4 hours.

EXAMPLE 8

54.8 g of DOPO, 6 g of formaldehyde, 0.3 g of tetrabutylammonium hydrogensulphate, 0.05 g of $K_2CO_3$ and 600 ml of ethanol were placed in a 1 liter reactor. The mixture is left to react for 4 hours under reflux, after which the ethanol is evaporated off under reduced pressure and the hydroxymethyl-dioctylphosphine oxide is recovered. 60 g of the hydroxymethyl-dioctylphosphine oxide obtained above, 700 g of sodium hydroxide pellets, 700 g of water, 600 ml of toluene and 1 g of TBAH are placed in a 2 liter reactor.

At an ambient temperature of 20° C., a solution of 30 g of p-chloromethylstyrene in 50 ml of toluene is added to the mixture, with stirring.

The mixture is left to react for 6 hours, with stirring, after which the reaction mixture is left to settle, the organic phase is recovered, filtered and dried over MgSO$_4$ and the toluene is evaporated off under reduced pressure.

This gives, with a yield of 93%, a product melting at 22° C. and identified as having the formula:

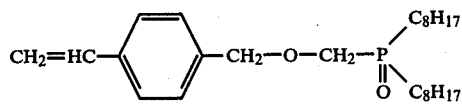

by the following spectra:

NMR: multiplet at 0.92 ppm (CH$_3$ of the octyls); broad signal at 1.27 ppm (CH$_2$ of the octyls); broad signal at 1.62 ppm (CH$_2$ in the α-position to the P); doublet at 3.70 ppm (CH$_2$ between P and O); singlet at 4.52 ppm (CH$_2$ between O and phenyl); multiplet at 5.45 ppm (vinyl CH$_2$); multiplet at 6.72 ppm (vinyl CH); broad signal at 7.30 ppm (aromatic H).

IR: Absorption of P=O group at 1,170–1,180 cm$^{-1}$; Absorption of CH$_2$OCH$_2$ group at 1,090 cm$^{-1}$.

We claim:

1. Process for the synthesis of a tertiary phosphine oxide of formula

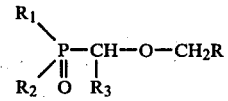

which consists of reacting an hydroxymethyl phosphine oxide with an halogenomethyl compound according to the reaction hereinbelow

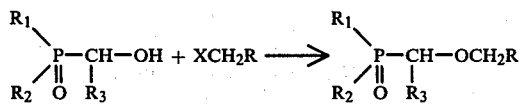

wherein
$R_1$ and $R_2$ are identical or different and are linear or branched alkyl of 1 to 18 carbon atoms or phenyl;
$R_3$ is H or a group of formula —CH$_2$R$_4$ in which R$_4$ is H, linear or branched alkyl of 1–11 carbon atoms or phenyl;
X is chlorine or bromine;
R is (a) a group of formula —CH=CHY in which Y is H, phenyl or —CH$_2$X in which X is chlorine or bromine; or
(b) R is

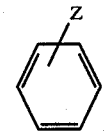

in which Z is H, an alkyl of 1 to 4 carbon atoms, vinyl, halogen, a group —CH$_2$X or a group

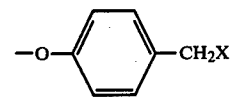

in which X is chlorine or bromine;
(c) R is alkyl of 1–12 carbon atoms, in a water-immiscible organic medium in an aqueous phase containing an inorganic base, and in the presence of a phase transfer catalyst, with stirring and isolating said tertiary phosphine oxide from the reaction mixture.

2. Process according to claim 1 wherein $R_3$ is H and $R_1$ and $R_2$ contain 1–12 carbon atoms.

3. The process according to claim 1 wherein said water immiscible organic medium is a common solvent for said hydroxymethyl phosphine oxide and said halogenomethyl compound.

4. The process according to claim 2 wherein R is an alkyl chain of 1 to 12 carbon atoms substituted by at least one nitrile or epoxy group.

5. Process according to claim 1, wherein the aqueous phase containing an inorganic base is an aqueous solution containing from 30 to 60% by weight of sodium hydroxide or potassium hydroxide.

6. Process according to claim 1, wherein the phase transfer catalyst is a member selected from the group consisting of the quaternary ammonium, phosphonium or arsonium salts of the general formula:

$$A_1A_2A_3A_4Y^+ . X^-$$

in which Y=N, P or As, $A_1$, $A_2$, $A_3$ and $A_4$ are identical or different and are $C_1$ to $C_8$ alkyl groups, benzyl groups or polymer chains, and $X^-$ is an anion.

7. Process according to claim 1 wherein the phase transfer catalyst is a member selected from the group consisting of polyethylene oxide, crown ethers and cryptands.

8. Process according to claim 1, wherein the reaction is carried out at between 40° and 70° C.

9. Process according to claim 1, wherein the ratio of the volume of aqueous phase to the volume of organic phase is between 5:1 and 1:10.

10. Process according to claim 1 wherein the concentration of the reactants in the organic phase is between 0.1 and 20%.

11. Process according to claim 1 wherein the proportion of phase transfer catalyst, relative to the halogenomethyl derivative, is between 1 and 10 mol %, preferably of the order of 5 mol %.

12. The process according to claim 11 wherein the proportion of phase transfer catalyst relative to the halogenomethyl compound is 5 mole %.

13. A tertiary phosphine oxide of formula

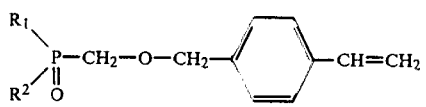

wherein $R_1$ and $R_2$ are the same or different and are linear or branched alkyl of 1 to 18 carbon atoms or phenyl.

14. The compound according to claim 13 which is di-n-octyl-(p-styryl)-methyloxy-methyl phosphine oxide.

15. A tertiary phosphine oxide according to claim 13, wherein $R_1$ and $R_2$ contain between 1 and 12 carbon atoms.

* * * * *